United States Patent [19]
Ludec

[11] 3,992,395
[45] Nov. 16, 1976

[54] PROCESS FOR THE PREPARATION OF CHLORINATED PHENYLHYDROXYLAMINES

[75] Inventor: Joel Le Ludec, Rhone, France
[73] Assignee: Rhone-Poulenc, S.A., Paris, France
[22] Filed: Nov. 25, 1974
[21] Appl. No.: 527,042

[30] Foreign Application Priority Data
Nov. 26, 1973   France .............................. 73.42008

[52] U.S. Cl. ...................... 260/307 A; 260/307 C; 260/580; 424/272
[51] Int. Cl.² ...................................... C07D 271/10
[58] Field of Search ............ 260/307 A, 580, 307 C

[56]   References Cited
UNITED STATES PATENTS

| | | | |
|---|---|---|---|
| 3,413,349 | 11/1968 | Bertsch et al. ...................... | 260/580 |
| 3,694,509 | 9/1972 | Rylander et al. ................... | 260/578 |
| 3,941,798 | 3/1976 | Fort et al. ....................... | 260/307 A |

FOREIGN PATENTS OR APPLICATIONS
271,527   5/1970   U.S.S.R.

*Primary Examiner*—Nicholas S. Rizzo
*Assistant Examiner*—Jose Tovar
*Attorney, Agent, or Firm*—Stevens, Davis, Miller & Mosher

[57] ABSTRACT

Chlorinated phenylhydroxylamines of the formula:

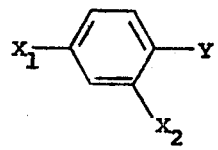

(wherein one of $X_1$ and $X_2$ represents chlorine and the other represents hydroxylamino, and Y represents chlorine or a 2-alkyl-1,3,4-oxadiazolin-5-one group attached through the 4-position nitrogen atom) are prepared by the hydrogenation, in the presence of a catalyst based on a metal selected from platinum, palladium, rhodium, ruthenium and nickel, of a nitrophenyl compound of the formula:

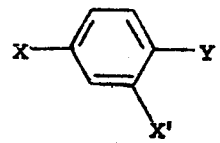

(wherein one of X and X' represents chlorine and the other represents nitro, and Y is as hereinbefore defined) and in the presence of a nitrogen-containing organic base, the ratio by weight of the organic base to the nitrophenyl compound being greater than 0.1. The products are inter alia useful as intermediates for the preparation of herbicides.

14 Claims, No Drawings

PROCESS FOR THE PREPARATION OF CHLORINATED PHENYLHYDROXYLAMINES

This invention relates to a process for the preparation of chlorinated phenylhydroxylamines by selective catalytic hydrogenation of nitrophenyl compounds.

It is known that during catalytic hydrogenation nitro compounds are converted in an intermediate stage to partially reduced derivatives, the most important of which are nitroso derivatives and hydroxylamines; however, these intermediate derivatives generally canot be isolated because they are rapidly reduced to the corresponding amines. In order to prepare certain hydroxylamines, it has been proposed to use, as the catayst, either palladium on charcoal [K. Brand and J. Steiner, Ber., 55, 875 (1922)], or freshly prepared and very carefully washed Raney nickel [A. Sugimori, Bull. Chem. Soc. Japan, 33, 1599 (1960)]. In each case it is, however, necessary to interrupt the reaction when the amount of hydrogen consumed corresponds to that which can be calculated from the stoichiometric requirements of the reaction. Other authors such as K. Taya [Chem. comm., 464-5 (1966)] have proposed the selective reduction of nitrobenzene, nitrotoluenes and nitrochlorobenzenes to hydroxylamines by means of a catalyst based on iridium or by means of a mixed iridiumplatinum catalyst. These catalysts lead to satisfactory selectivity but the rate of hydrogenation is slow.

The catalysts based on platinum generally reduce the nitro derivatives to the final stage of hydrogenation, namely the amine. Thus, when nitrobenzene is reduced with a platinium-based catalyst prepared according to the Adam method aniline is essentially obtained, even if the reaction is interrupted after the theoretical amount of hydrogen has been consumed (K. Taya; loc. cit.).

A process has now been found, and it is this which forms the subject of the present invention, for the preparation of chlorinated phenylhydroxylamines of the formula:

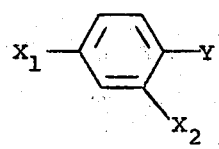

wherein one of the symbols $X_1$ and $X_2$ represents a chlorine atom and the other represents a hydroxylamino group (i.e. HONH—), and Y represents a chlorine atom or a dihydrooxadiazolyl group of the formula:

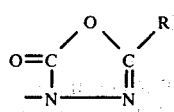

wherein R represents a straight- or branched-chain alkyl radical containing 1 to 4 carbon atoms.

The process of the present invention comprises the hydrogenation, in the presence of a catalyst based on a metal selected from platinum, palladium, rhodium, ruthenium and nickel, of a nitrophenyl compound of the general formula:

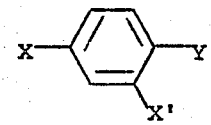

(wherein one of the symbols X and X' represents a chlorine atom and the other represnts a nitro group and Y is as hereinbefore defined) in the presence of a nitrogen-containing organic base selected from secondary or tertiary mono-amines with alkyl or cycloalkyl substituent groups on the amino radical; pyrrolidine and pyrrolidines which are alkylated on the nitrogen atom and/or on one or more of the carbon atoms of the ring; piperidine and piperidines which are N-alkylated and optionally alkylated on one or more of the carbon atoms of the ring; aniline and anilines which are N-alkylated and/or cycloalkylated, and optionally alkylated on one or more of the carbon atoms of the ring, and pyridine, alkylated pyridines, quinoline and isoquinoline, the ratio by weight of the organic base to the nitro-phenyl compound being greater than 0.1.

The nitrophenyl compounds which are hydrogenated according to the process of the invention are nitrodichlorobenzenes and nitrochlorophenyloxadiazolinones. Nitrochlorophenyloxadiazolinones are, for example, described in British patent specification No. 1286067.

The use of the nitrogen-containing organic base during the hydrogenation of the nitrophenyl compounds of general formula III makes it possible to stop the reaction at the hydroxylamine stage. The amount of organic base employed must be sufficient to provide the selectivity. In particular, it has been found that the use of a base in trace amounts does not make it possible to restrict the hydrogenation to the hydroxylamine stage. The amount of base employed must be such that the ratio by weight of nitrogen-containing organic base to nitro compound is greater than 0.1 and preferably between 0.5 and 5, the upper limit not being critical.

The secondary or tertiary mono-amines generally carry alkyl substituents with 1 to 6 carbon atoms or cyclohexyl or cyclopentyl groups, for example diethylamine, dibutylamine, diisopropylamine, triethylamine or dicyclohexylamine.

The alkylated pyrrolidines and piperidines generally carry one or two alkyl groups with 1 to 4 carbon atoms attached to the nitrogen atom and/or to the carbon atoms of the ring, examples of such substituted compounds being N-butylpiperidine, N-ethylpiperidine, N-methylpiperidine, 1,2-dimethylpiperidine, 1-ethyl-2-methylpiperidine, N-methylpyrrolidine, 2-ethylpyrrolidine, N-butylpyrrolidine, 1-ethyl-2-methylpyrrolidine and 1,2-dimethylpyrrolidine.

The N-alkylated or N-cycloalkylated anilines generally carry one or two alkyl groups with 1 to 4 carbon atoms or cyclopentyl or cyclohexyl groups attached to the nitrogen atom. These anilines can optionally carry an alkyl substituent on a carbon atom of the ring, the said alkyl substituent containing 1 to 4 carbon atoms. The following substituted aniline compounds are mentioned by way of illustration: N-methylaniline, N-ethylaniline, N-butylaniline, N-cyclohexylaniline, N- butyl-N-methylaniline, N,N-dimethylaniline, N,N-dibutylaniline and N,2-(or N,3-)dimethylaniline.

The alkylated pyridines which are preferentially used carry one or two alkyl substituents with 1 to 4 carbon atoms, for example 2-(or 3-) (or 4-)methyl-pyridine, 2-(or 3-)(or 4-)ethyl-pyridine, 2-(or 3-)(or 4-)butyl-pyridine, 2,3-(or 2,5-)(or 2,4-)dimethyl-pyridine and 3-ethyl-5-(or 6-)methyl-pyridine.

Amongst the various nitrogen-containing organic bases which have just been described, pyridine, alkyl-pyridines, aniline, alkylated and/or cycloalkylated anilines, quinoline and isoquinoline are advantageously employed.

The hydrogenation catalyst is based on platinum, palladium, rhodium, ruthenium or nickel, which may or may not be deposited on a support. As a general rule, when a catalyst based on a precious metal is used, it is preferable to employ a catalyst deposited on a support in order to achieve maximum activity for a given amount of active metal. Amongst the supports, porous or nonporous carbon blacks of small or large specific surface area, alumina, calcium carbonate and barium sulphate may be mentioned by way of illustration. The concentration of the precious metal on its support is not critical, the concentration, expressed by weight, is generally between 0.1 and 15%, preferably between 0.5 and 10%. The amount of precious metal used is such that it is generally between 0.001 and 1% of the weight of the nitrophenyl compound employed in the reaction; preferably it is between 0.01% and 0.1% of the weight of the nitrophenyl compound.

When nickel is used is the catalyst, it is conveniently employed in the form of Raney nickel. The amount of nickel is such that it is generally between 0.5 and 20%, and preferably between 3 and 10%, of the weight of the nitrophenyl compound employed in the reaction.

The selective hydrogenation reaction can be carried out at a temperature between 0° and 100° C., and preferably between 20° and 50° C. The hydrogen pressure employed, which is generally chosen as a function of the reaction temperature, must be such that the rate of the reaction is sufficiently rapid, whilst avoiding a side reaction involving the hydrogenation of the phenylhydroxylamines to amines. As a general rule, the hydrogen pressure is between 1 to 50 atmospheres.

An organic diluent can be added to the reaction medium. For example, alcohols containing up to 4 carbon atoms such as ethanol or methanol, and aliphatic or aromatic hydrocarbons such as hexane or toluene may be mentioned by way of illustration.

The process according to the invention makes it possible to obtain 2,5-dichlorophenylhydroxylamine and 3,4-dichlorophenylhydroxylamine of the formulae:

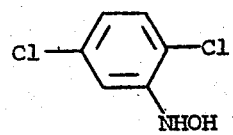

IV and

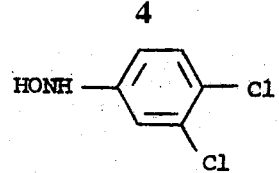

V

The process of the invention also makes it possible to prepare the 4-(hydroxyaminochlorophenyl)-1,3,4-oxadiazolinones of the formulae:

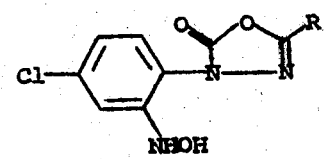

VI and

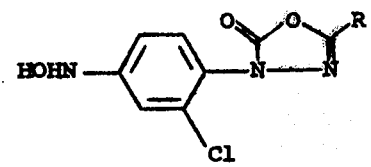

VII wherein R is as hereinbefore defined. The (4-hydroxyamino-2-chlorophenyl)-1,3,4-oxadiazolinones of formula VII are new compounds and as such constitute a further feature of the present invention.

The compounds of formula I prepared according to the process of the present invention are useful intermediates and can, for example, be converted readily by means of the Bamberger rearrangement to aminochlorophenols and to amino-hydroxy-chlorophenyl-oxadiazolinones. The replacement in the aforesaid amino compounds of the amino group by a chlorine atom, by the application of known procedures, makes it possible to obtain substituted dichlorophenols such as, for example, compounds of the formula:

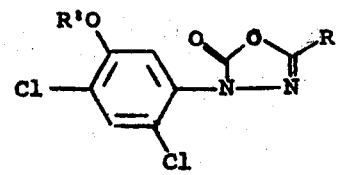

VIII wherein R' represents a hydrogen atom or a straight- or branched-chain alkyl group containing 1 to 4 carbon atoms and R is as hereinbefore defined. Such compounds are described, for example, in British patent specification No. 1286067 and are useful as herbicides.

The following Examples illustrate the invention.

EXAMPLE 1

2-t.-Butyl-4-(2-nitro-4-chlorophenyl)-1,3,4-oxadiazolin-5-one (14.88 g.), a catalyst based on platinum (0.156 g.; platinum deposited to the extent of 4.76% by weight on carbon black of specific surface area 900 m²/g.) and pyridine (45 cc.) are introduced into an autoclave. Hydrogenation is carried out over the course of 40 minutes, at 25° C., under an absolute pressure of 10 bars of hydrogen.

After filtering off the catalyst under a nitrogen atmosphere, the pyridine is completely removed from the filtrate by distillation, and 2-t.-butyl-4-(2-hydroxyamino-4-chlorophenyl)-1,3,4-oxadiazolin-5-one (14.19 g.) of the formula:

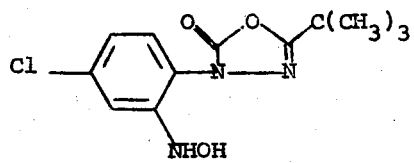

is obtained. (Melting point: 190° C., IR and NMR spectra in agreement).

EXAMPLE 2

The nitrophenyl starting material of Example 1 (14.88 g.), a catalyst based on palladium (0.149 g.; palladium deposited to the extent of 10% by weight on carbon black of spcific surface area 900 m²/g.) and pyridine (45 ml.) are introduced into an autoclave. Hydrogenation is carried out over the course of 20 minutes, at 25° C., under an absolute pressure of 15 bars of hydrogen.

After treatment of the reaction mixture similar to that of the preceding example, 2-t.-butyl-4-(2-hydroxyamino-4-chloropheyl)-1,3,4-oxadiazolin-5-one (14.08 g.) is obtained.

EXAMPLE 3

The nitrophenyl starting material of Example 1 (14.88 g.), Raney nickel (0.73 g.) and pyridine (45 ml.) are introduced into an autoclave. Hydrogenation is carried out over the course of 57 minutes, at 25° C., under 5 bars of hydrogen.

After treatment of the reaction mixture similar to that of Example 1 2-t.-butyl-4-(2-hydroxyamino-4-chlorophenyl)-1,3,4-oxadiazolin-5-one (14.02 g.) is obtained.

EXAMPLE 4

The nitrophenyl starting material of Example 1 (14.88 g.), a catalyst based on platinum (0.157 g.; the same as used in Example 1) and aniline (55 ml.) are introduced into an autoclave. Hydrogenation is carried out over the course of 2 hours 10 minutes, at 25° C., under an absolute pressure of 10 bars of hydrogen.

The hydroxylamine formed is insoluble in the medium. After filtration, the hydroxylamine-catalyst mixture is washed with acetonitrile. Filtration is again carried out. The acetonitrile, which contains the hydroxylamine, is evaporated to give 2-t.-butyl-4-(2-hydroxyamino-4-chlorophenyl)-1,3,4-oxadiazolin-5-one (11.58 g.).

EXAMPLE 5

The nitrophenyl starting material of Example 1 (14.88 g.), a platinum-based catalyst (0.157 g; the same as used in Example 1) and N,N-dimethylaniline (55 ml.) are introduced into the autoclave. Hydrogenation is carried out over the course of 55 minutes, at 25° C., under an absolute pressure of 10 bars.

The hydroxylamine is insoluble in dimethylaniline. After treatment of the reaction mixture as described in Example 4, 2-t.-butyl-4-(2-hydroxyamino-4-chlorophenyl)-1,3,4-oxadiazolin-5-one (11.58 g.) is obtained.

EXAMPLE 6

2,5-Dichloro-nitrobenzene (4.78 g.), pyridine (24.39 g.) and a catalyst of platinum on carbon black (0.052 g.; the same as used in Example 1) are introduced into an autoclave. Hydrogenation is carried out over the course of 1 hour, at 25° C., under an absolute pressure of 15 bars.

The catalyst is filtered off. From 25.35 g. of the filtrate, the pyridine is evaporated. To the resulting oil, hexane (15 ml.) cooled to 0° C. is added. After filtration, 2,5-dichlorophenylhydroxylamine (3.86 g.) (Melting point: 124° C.) is obtained.

EXAMPLE 7

7.44 g. of 2-t.-butyl-4-(2-chloro-4-nitrophenyl)-1,3,4-oxadiazolin-5-one, a catalyst based on platinum (0.07 g.; the same as used in Example 1) and pyridine (25 ml.) are introduced into an autoclave. Hydrogenation is carried out over the course of 50 minutes, at 25° C., under an absolute pressure of 10 bars.

After filtering off the catalyst and evaporating the pyridine from the filtrate, the residue is taken up in methanol (100 ml.) and the hydroxylamine product is precipitated by addition of ice-water (500 ml.). After filtering and drying, 2-t.-butyl-4-(2-chloro-4-hydroxyaminophenyl)-1,3,4-oxadiazolin-5-one (6.31 g.) of the formula:

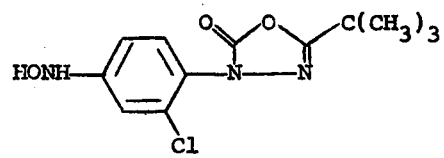

is obtained. Its melting point is 138° C.; IR and NMR spectra in agreement.

I claim:

1. Process for the preparation of a chlorinated phenylhydroxylamine of the formula:

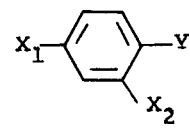

wherein one of $X_1$ and $X_2$ represents chlorine and the other represents hydroxylamino, and Y represents chlorine or a dihydrooxadiazolyl group of the formula:

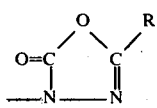

wherein R represents alkyl of 1 through 4 carbon atoms, which consists essentially of the hydrogenation, at between 0° and 100° C and under a hydrogen pressure of 1 to 50 atmospheres in the presence of a catalyst consisting of platinum, palladium, rhodium, ruthenium or nickel, of a nitrophenyl compound of the formula:

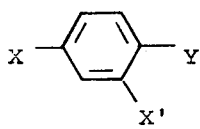

wherein one of X and X' represents chlorine and the other represents nitro, and Y is as hereinbefore defined, in the presence of, as the sole diluent, aniline, n-cyclopentyl or cyclohexyl aniline, N-Alkylated Anilines, Anilines alkylated on at least one the carbon atoms of the ring, pyridine, alkylated pyridines, quinoline or isoquinoline, the alkyls of the said alkylated anilines and pyridines having 1 through 4 carbon atoms the ratio by weight of the said organic base to the nitrophenyl compound being greater than 0.1, and the proportion by weight of the said catalyst being between 0.001 and 1% by weight of the nitrophenyl phenyl compound initially present when a precious metal catalyst is used and between 0.5 and 20% by weight of the nitrophenyl compound when a nickel catalyst is used.

2. Process according to claim 1 in which the hydrogenation temperature is between 20° and 50° C.

3. Process according to claim 1 in which the ratio by weight of the said organic base to the nitrophenyl compound is between 0.5 and 5.

4. A 1,3,4-oxadiazolinone of the formula:

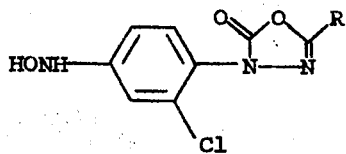

wherein R represents alkyl of 1 through 4 carbon atoms.

5. The 1,3,4-oxadiazolinone according to claim 4 which is 2-t.-butyl-4-(2-chloro-4-hydroxyaminophenyl)-1,3,4-oxadiazolin-5-one.

6. Process according to claim 1 in which the catalyst is a precious metal and the amount of precious metal catalyst is between 0.01% and 0.1% by weight of the nitrophenyl compound initially present.

7. Process according to claim 1 in which the catalyst is nickel and the amount of nickel is between 3 and 10% by weight of the nitrophenyl compound initially present.

8. Process according to claim 1 wherein a 2-alkyl-4-(2-nitro-4-chlorophenyl)-1,3,4-oxadiazolin-5-one in which the alkyl is of 1 through 4 carbon atoms is hydrogenated in the presence of a platinum catalyst and pyridine.

9. Process according to claim 1 wherein a 2-alkyl-4-(2-nitro-4-chlorophenyl)-1,3,4-oxadiazolin-5-one in which the alkyl is of 1 through 4 carbon atoms is hydrogenated in the presence of a palladium catalyst and pyridine.

10. Process according to claim 1 wherein a 2-alkyl-4-(2-nitro-4-chlorophenyl)-1,3,4-oxadiazolin-5-one in which the alkyl is of 1 through 4 carbon atoms is hydrogenated in the presence of a Raney nickel catalyst and pyridine.

11. Process according to claim 1 wherein a 2-alkyl-4-(2-nitro-4-chlorophenyl)-1,3,4-oxadiazolin-5-one in which the alkyl is of 1 through 4 carbon atoms is hydrogenated in the presence of a platinum catalyst and aniline.

12. Process according to claim 1 wherein a 2-alkyl-4-(2-nitro-4-chlorophenyl)-1,3,4-oxadiazolin-5-one in which the alkyl is of 1 through 4 carbon atoms is hydrogenated in the presence of a platinum catalyst and N,N-dimethylaniline.

13. Process according to claim 1 wherein a 2,5-dichloronitrobenzene is hydrogenated in the presence of a platinum catalyst and pyridine.

14. Process according to claim 1 wherein a 2-alkyl-4-(2-chloro-4-nitrophenyl)-1,3,4-oxadiazolin-5-one in which the alkyl is of 1 through 4 carbon atoms is hydrogenated in the presence of a platinum catalyst and pyridine.

* * * * *